United States Patent
Liles

Patent Number: 6,121,404
Date of Patent: Sep. 19, 2000

[54] β-DIKETO FUNCTIONAL ORGANOSILICON COMPOUNDS

[75] Inventor: Donald Taylor Liles, Midland, Mich.

[73] Assignee: Dow Corning Corporation, Midland, Mich.

[21] Appl. No.: 09/110,281

[22] Filed: Jul. 6, 1998

[51] Int. Cl.[7] .................................................... C08G 77/00
[52] U.S. Cl. .......................... 528/41; 524/588; 528/21; 528/26; 528/34; 528/38; 556/418; 556/419; 556/422; 556/439
[58] Field of Search ................................. 528/26, 38, 21, 528/34, 41; 556/418, 419, 422, 439; 524/588

[56] References Cited

U.S. PATENT DOCUMENTS

| | | | |
|---|---|---|---|
| 4,861,839 | 8/1989 | Mizuguchi et al. | 525/506 |
| 5,025,053 | 6/1991 | Canivenc | 524/265 |
| 5,952,443 | 9/1999 | Wilt et al. | 528/26 |

*Primary Examiner*—Melvyn I. Marquis
*Assistant Examiner*—Jeffrey B. Robertson
*Attorney, Agent, or Firm*—James L. DeCesare

[57] ABSTRACT

A method of making β-diketo functional silanes and siloxanes in which the acetoacetic ester moiety, i.e., β-diketo $CH_3COCH_2CO$—, is attached to the oxygen or nitrogen atoms of C—OH or C—$NH_2$ containing functional silanes or siloxanes, by reacting the organosilicon nucleophile with diketene, as illustrated below for the C—OH containing functional silane.

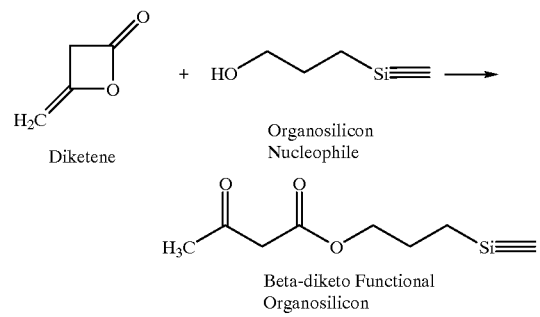

The products can be formed into curable compositions, or used as additives in durable textile treatments, polyurethane foams, and hair care applications.

6 Claims, No Drawings

β-DIKETO FUNCTIONAL ORGANOSILICON COMPOUNDS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to new β-diketo functional organosilicon compounds, and to a method of making the β-diketo functional organosilicon compounds.

BACKGROUND OF THE INVENTION

While the prior art discloses certain dibenzoylmethane containing organopolysiloxanes that include a β-diketo moiety, i.e., U.S. Pat. No. 5,025,053 (Jun. 18, 1991), the dibenzoylmethane containing organopolysiloxanes described in the '053 patent are not the same as the β-diketo functional organosilicon compounds described herein; nor is the method of making dibenzoylmethane containing organopolysiloxanes in the '053 patent similar to the method of making β-diketo functional organosilicon compounds according to the present invention.

BRIEF SUMMARY OF THE INVENTION

This invention relates to a method of making a β-diketo functional organosilicon compound by reacting diketene or an equivalent acetoacetoxylating agent such as the adduct of diketene and acetone with an organosilicon nucleophile containing in its molecule a C—OH or a C—NH$_2$ moiety.

This invention also relates to β-diketo functional organosilicon compounds prepared according to this method; as well as to an elastomeric film prepared by (i) dissolving a β-diketo functional organosilicon compound in water to form a solution, (i) adding an amine functional siloxane to the solution, and (iii) removing the water.

The organosilicon nucleophile is preferably a hydroxyl functional siloxane polymer or oligomer a hydroxyorganosilane, a hydroxyl functional silicone polyether, an amine functional siloxane polymer, or an aminoorganosilane.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

The present invention describes new organosilicon compositions including silanes and siloxanes having β-diketo functionality. The compositions are easy to prepare, and since the compositions are reactive, they offer utility in a wide variety of applications.

In particular, β-diketo functional siloxanes can be prepared by reacting as one component, a hydroxyl functional silicone polyether such as HO—(EtO)$_n$—(CH$_2$)$_3$—(OSiMe$_2$)$_m$—(CH$_2$)$_3$—(OEt)$_n$—OH, wherein n represents 0 to 100, m represents 1 to 1000, Et is —CH$_2$CH$_2$—, and Me is —CH$_3$. While it is most preferred that n be at least one, i.e., n=1–100, in some cases it may be desirable to prepare β-diketofunctional siloxanes without polyether groups, such that n would be equal to zero.

Such hydroxyl functional silicone polyethers are shown below in more detail.

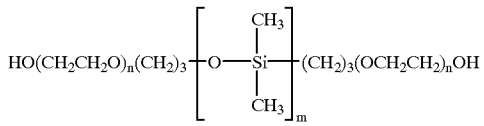

This hydroxyl functional silicone polyether can be reacted with diketene shown below.

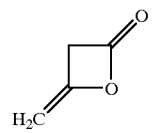

to produce a product represented by the formula:

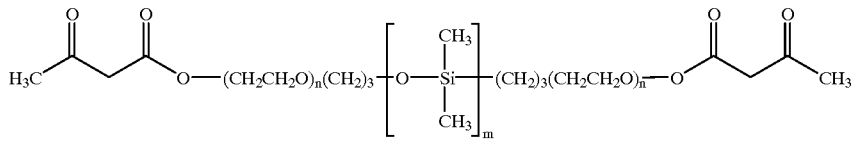

β-diketo functional siloxanes can also be prepared by reacting diketene with a hydroxyl functional silicone polyether such as Me$_3$Si—(OSiMe$_2$)$_x$(OSiMe(CH$_2$)$_3$—(OEt)$_n$—OH)$_y$—SiMe$_3$, wherein n represents 0 to 100, most preferably 1 to 100, x is 0 to 1000, and y is 1–1000. Et and Me have the same meaning as above.

Such hydroxyl functional silicone polyethers are shown below in more detail.

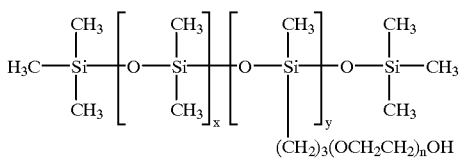

When a hydroxyl functional silicone polyether of this type is reacted with diketene, the result is the product shown below.

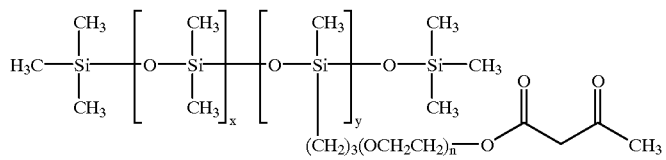

β-diketo functional silanes can be prepared by reacting diketene with an hydroxyorganosilane. For example, one convenient route to an hydroxyorganosilane suitable for conversion to a β-diketo functional silane, involves the reaction of an epoxide functional silane such as 3-glycidoxypropyltrimethoxysilane, with a hydroxyl functional amine such as diethanol amine, and this reaction is shown below.

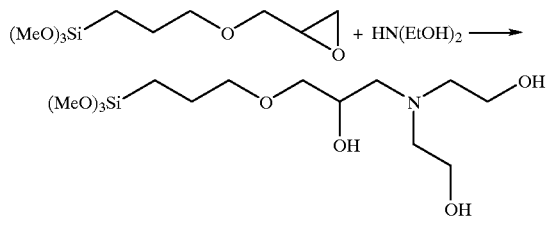

Shortly after formation, the hydroxyl functional silane compound prepared as shown above from 3-glycidoxypropyltrimethoxysilane and diethanol amine, can be reacted with either diketene or an equivalent acetoacetoxylating agent, and this reaction is shown below.

It should be understood that either all of hydroxyls or only a portion of hydroxyls can be acetoacetoxylated, and this is dependent upon what stoichiometric ratios of acetoacetoxylating agent to equivalents of hydroxyls are employed.

Some examples of suitable hydroxyorganosilanes which can be employed in the reaction are:

(hydroxypropyl)trimethylsilane $HO(CH_2)_3Si(CH_3)_3$
(2-hydroxyethyl)trimethylsilane $HOCH_2CH_2(CH_3)_3Si$;
(2-hydroxyethyl)diphenylmethylsilane $HOCH_2CH_2(C_6H_5)_2(CH_3)Si$;

as well as compounds having the formulas $(HOCH_2)_2(CH_3)_2Si$, $HOCH_2(CH_2)_2(CH_3)_3Si$, $(HOCH_2CH_2CH_2)_2(CH_3)_2Si$, $HOCH_2(CH_2)_3(CH_3)_3Si$, and $HOCH_2(CH_2)_4(CH_3)_3Si$.

Thus, the acetoacetic ester moiety, i.e., β-diketo $CH_3COCH_2CO-$, can be attached respectively to either the oxygen or nitrogen atoms of $\equiv C-OH$ or $\equiv C-NH_2$ containing functional silanes and siloxanes, by reacting the

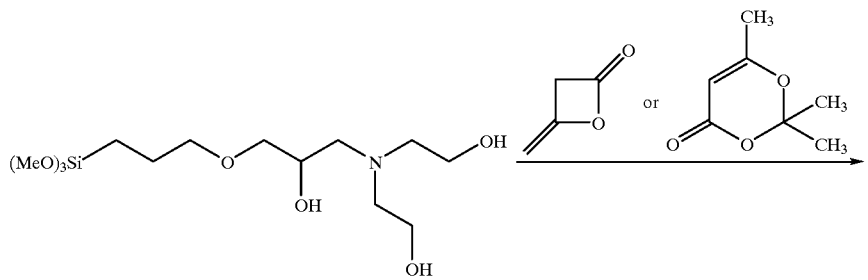

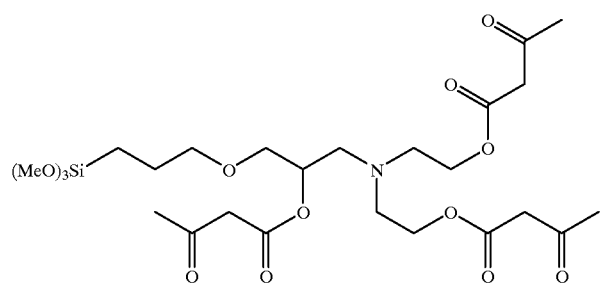

corresponding organosilicon nucleophile, with diketene as depicted below.

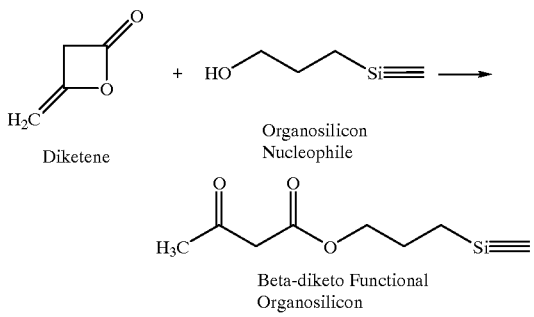

In this regard, it should be noted that amines are generally sufficiently nucleophilic to react with diketene on their own. Alcohols, however, generally less nucleophilic, may require a catalyst such as triethylamine $(C_2H_5)_3N$. In either case, the reaction can be performed in the presence of water.

Although diketene is suitable for use in the process of the present invention, it may be more convenient to employ the diketene acetone adduct rather than diketene. The diketene acetone adduct, i.e., 2,2,6-trimethyl-4H-1,3-dioxin-4-one, has the structure:

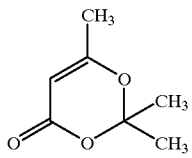

Another convenient transacetoacetoxylating agent is tert-butyl acetoacetate (tert-BAA). In this regard, it should be noted that tert-BAA undergoes a dissociation at 120–160° C. to produce tert-butyl alcohol and acetyl ketene, the latter of which reacts with the hydroxyls or other nucleophiles to convert them to acetoacetate groups. The structure of tert-BAA is shown below.

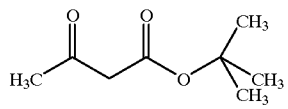

It is also possible to carry out transacetoacetoxylating reactions according to this invention by using methyl acetoacetate $CH_3COCH_2CO_2CH_3$ or ethyl acetoacetate, i.e., acetoacetic ester $CH_3COCH_2CO_2C_2H_5$, but the diketene acetone adduct and tert-BAA are more convenient to employ, and therefore are the most preferred acetoacetoxylating agents.

Because the acetoacetic ester group has two distinct reactive sites, it is capable of undergoing a variety of useful reactions. Thus, it can react with melamine-formaldehyde resins and isocyanates. It can also react with aldehydes and can participate in Michael addition reactions. Furthermore, it can react via the ketone carbonyl with amines to form enamines. In addition, it can form chelates with polyvalent ions. All of these types of reactions can be utilized to prepare crosslinked polymers in which the beta-diketo functional silicones described herein can be employed. For example, crosslinking via enamine formation is depicted below with an aminoorganosilicon compound, wherein R represents an alkyl group such as methyl.

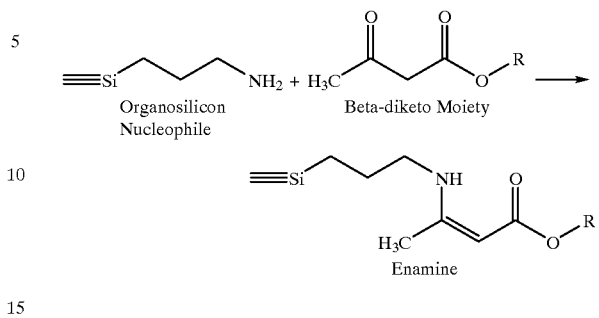

Amine functional siloxane polymers which can be employed as organosilicon nucleophiles for reacting with diketene have the formula:

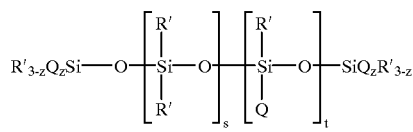

wherein R' denotes an alkyl group of 1 to 4 carbons or a phenyl group, with the proviso that at least 50 percent of the total number of R' groups are methyl; Q denotes an amine functional substituent of the formula —R" Z wherein R" is a divalent alkylene radical of 3 to 6 carbon atoms, and Z is a monovalent radical such as —NR$_2$''' and —NR'''$(CH_2)_p$NR$_2$''', wherein R''' denotes hydrogen or an alkyl group of 1 to 4 carbons.

In the formula, p is a positive integer having a value of 2 to 6; z has a value of 0 or 1; s has an average value of 25 to 3000; t has an average value of 0 to 100 when z is 1, t has an average value of 1 to 100 when z is 0; with the proviso that in all cases t has an average value that is not greater than one tenth the average value of s.

Suitable R' groups may be independently selected from among methyl, ethyl, propyl, isopropyl, butyl, isobutyl, and phenyl, with the proviso that at least fifty percent of the R' groups are methyl.

Alkylene radicals represented by R" include trimethylene, tetramethylene, pentamethylene, —CH$_2$CHCH$_3$CH$_2$—, and —CH$_2$CH$_2$CHCH$_3$CH$_2$—. Siloxanes where R" is trimethylene or an alkyl substituted trimethylene radical such as —CH$_2$CHCH$_3$CH$_2$— are preferred.

Alkyl groups of 1 to 4 carbon atoms represented by R''' include methyl, ethyl, propyl, isopropyl, butyl, and isobutyl.

Useful Z radicals include the unsubstituted amine radical —NH$_2$, alkyl substituted amine radicals such as —NHCH$_3$, —NHCH$_2$CH$_2$CH$_2$CH$_3$, and —N(CH$_2$CH$_3$)$_2$; and aminoalkyl substituted amine radicals such as —NHCH$_2$CH$_2$NH$_2$, —NH(CH$_2$)$_6$NH$_2$, and —NHCH$_2$CH$_2$CH$_2$N(CH$_3$)$_2$.

When z is zero, the silicone polymer has only pendent amine functional substituents in the polymer chain. When z is one, the silicone polymer may have only terminal amine functional substituents, or both terminal and pendent amine functional substituents in the polymer chain.

Preferably, s may vary from 25 to 100, and t may vary from zero to 100 when z is one, and from one to 100 when z is zero. Most preferably, the value of s+t should be in the range of about 50 to 500.

Examples of aminoorganosilanes which can be employed as the organosilicon nucleophile in this invention are:

4-aminobutyltriethoxysilane H$_2$NCH$_2$CH$_2$CH$_2$CH$_2$Si(OC$_2$H$_5$)$_3$;

N-(2-aminoethyl)-3-aminopropyltrimethoxysilane H$_2$NCH$_2$CH$_2$NHCH$_2$CH$_2$CH$_2$Si(OCH$_3$)$_3$;

N-(6-aminohexyl)aminopropyltrimethoxysilane H$_2$N(CH$_2$)$_6$NHCH$_2$CH$_2$CH$_2$Si(OCH$_3$)$_3$;

3-aminopropyldimethylethoxysilane H$_2$NCH$_2$CH$_2$CH$_2$(CH$_3$)$_2$Si(OC$_2$H$_5$);

3-aminopropylmethyldiethoxysilane H$_2$NCH$_2$CH$_2$CH$_2$(CH$_3$)Si(OC$_2$H$_5$)$_2$;

3-aminopropyltriethoxysilane H$_2$NCH$_2$CH$_2$CH$_2$Si(OC$_2$H$_5$)$_3$;

3-aminopropyltrimethoxysilane H$_2$NCH$_2$CH$_2$CH$_2$Si(OCH$_3$)$_3$;

3-aminopropyltris(methoxyethoxy-ethoxy)silane H$_2$NCH$_2$CH$_2$CH$_2$Si(OCH$_2$CH$_2$OCH$_2$CH$_2$OCH$_3$)$_3$;

aminoisobutyltrimethoxysilane; and
aminoisobutylmethyldimethoxysilane.

EXAMPLES

The following examples are set forth to illustrate the invention in more detail.

Example 1

40 g of a hydroxyl functional silicone polyether having the composition HO—(EtO)$_{12}$—(CH$_2$)$_3$—(OSiMe$_2$)$_{13}$—(CH$_2$)$_3$—(EtO)$_{12}$—OH, where Me represents —CH$_3$ and Et represents —CH$_2$CH$_2$—, was weighed into a jar, and to the hydroxyl functional silicone polyether was added 4.5 g of 2,2,6-trimethyl-4H-1,3-dioxin-4-one, i.e., diketene acetone adduct. The mixture was shaken for several minutes until a solution resulted, and 0.1 g of triethylamine was added to the solution followed by shaking. The mixture was allowed to remain undisturbed for 24 hours to ensure a complete reaction. A structural representation of the compound produced is shown below.

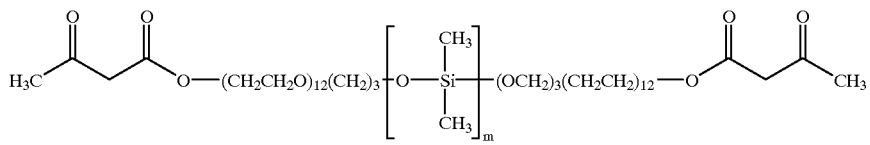

Example 2

An approximately 10 percent aqueous solution of the product prepared in Example 1 was made by dissolving 2 g of the product in 18 g of deionized water. To the solution was added an equivalent amount of an amine functional siloxane in the form of an aqueous emulsion. The particular amine functional siloxane used was a methoxy and isodecyl terminated methyl(aminoethylaminoisobutyl) dimethylpolysiloxane copolymer having a viscosity of about 1500 centistoke (mm$^2$/s). When water was removed, an elastomeric film was formed.

Example 3

25 g of 3-glycidyoxypropyltrimethoxysilane was weighed into a 4 ounce jar followed by 11.15 g of diethanol amine. The jar was capped and installed on a laboratory wrist shaker. The contents of the jar became opaque immediately upon shaking, but after two hours of shaking, the contents turned into a completely clear liquid. The jar was shaken for an additional hour for a total of three hours. A 25 g aliquot of the reaction mixture was weighed into a 4 ounce jar, followed by the addition of 36.7 g of 2,2,6-trimethyl-4H-dioxin-4-one. The bottle was shaken and allowed to remain undisturbed for 24 hours. The compound formed is shown below.

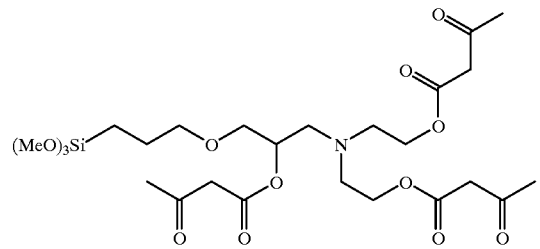

Example 4

The solution described in Example 3 was kept at ambient temperature for two months and observed from time to time. It remained a liquid without any appreciable change in appearance or viscosity. In contrast, a reaction product of 3-glycidyoxypropyltrimethoxysilane and diethanol amine to which no acetoacetoxylating agent such as 2,2,6-trimethyl-4H-dioxin-4-one had been added, gelled after two days, and formed a solid which was insoluble in water.

Example 5

0.5 g of the solution described in Example 3, i.e., an acetoacetoxylated hydroxy functional silane prepared by adding 2,2,6-trimethyl-4H-dioxin-4-one to the reaction product of 3-glycidyoxypropyltrimethoxysilane and diethanol amine, was added to 1.0 g of an aminofunctional siloxane polymer having a viscosity of 1500 centistoke and a nitrogen content of 0.36% by weight. The polymer had the structure R—(OSiMe$_2$)$_n$(OSiMeCH$_2$CH$_2$CH$_2$NH$_2$)$_m$—OR where R represents C$_2$H$_5$ and Me represents methyl. The mixture was stirred for several minutes to effect a solution, and allowed to remain undisturbed for 2 days at ambient laboratory temperature. At the end of two days, the liquid mixture had become an elastomer that was insoluble in toluene.

Example 6

0.25 g of the solution described in Example 3, i.e., an acetoacetoxylated hydroxyl functional silane prepared by adding 2,2,6-trimethyl-4H-dioxin-4-one to the reaction product of 3-glycidyoxypropyltrimethoxysilane and diethanol amine, was added to 1.0 g of an aqueous emulsion. The emulsion had an active content of 50% by weight of an aminofunctional siloxane polymer having a viscosity of 1500 centistoke and a nitrogen content of 0.62% by weight. The polymer had the structure R—(OSiMe$_2$)$_n$ $(OSiMeCH_2CH_2CH_2NHCH_2CH_2NH_2)_m$—OR where R represents $C_{11}H_{23}$ and Me represents methyl. The mixture was stirred for several minutes and allowed to remain undisturbed at ambient laboratory conditions. After three days, the mixture was inspected and found to be an elastomer which was insoluble in toluene. An aliquot of the aqueous aminofunctional siloxane alone was also allowed to dry under the same conditions, but it did not form an elastomeric film.

The β-diketo functional silanes and siloxanes of this invention are useful in a variety of industrial and commercial applications because of their reactivity. For example, they can be formed into curable compositions as shown in Example 2; they can be used in durable textile treatments; they possess utility in polyurethane foams as an additive; and they can be used in the personal care arena in hair care applications.

Other variations may be made in compounds, compositions, and methods described herein without departing from the essential features of the invention. The embodiments of the invention specifically illustrated herein are exemplary only, and are not intended as limitations on their scope except as defined in the appended claims.

I claim:

1. A method of making a β-diketo functional organosilicon compound comprising reacting diketene or equivalent acetoacetoxylating agent with an organosilicon nucleophile in which the organosilicon nucleophile is a hydroxyorganosilane selected from the group consisting of (hydroxymethyl)trimethylsilane $HOCH_2(CH_3)_3Si$;

(2-hydroxyethyl)trimethylsilane $HOCH_2CH_2(CH_3)_3Si$;

(2-hydroxyethyl)diphenylmethylsilane $HOCH_2CH_2(C_6H_5)_2(CH_3)Si$; and compounds having the formulas $(HOCH_2)_2(CH_3)_2Si$, $HOCH_2(CH_2)_2(CH_3)_3Si$, $(HOCH_2CH_2CH_2)_2(CH_3)_2Si$, $HOCH_2(CH_2)_3(CH_3)_3Si$, and $HOCH_2(CH_2)_4(CH_3)_3Si$.

2. A method according to claim 1 in which the equivalent acetoacetoxylating agent is selected from the group consisting of diketene acetone adduct, methyl acetoacetate, ethyl acetoacetate, and tert-butyl acetoacetate.

3. A method according to claim 1 in which the organosilicon nucleophile, diketene or equivalent acetoacetoxylating agent, are reacted in the presence of a catalyst.

4. A β-diketo functional organosilicon compound prepared according to the method defined in claim 1.

5. A β-diketo functional organosilicon compound comprising (i) the product obtained by reacting a glycidoxypropyl functional silane or a glycidoxypropyl functional siloxane with an hydroxyl functional amine compound having at least one hydrogen bonded to nitrogen, and reacting (i) with (ii) diketene or an equivalent acetoacetoxylating agent.

6. An elastomeric film prepared by (i) dissolving a β-diketo functional organosilicon compound in water to form a solution, (ii) adding an amine functional siloxane to the solution, and (iii) removing the water, the β-diketo functional organosilicon compound being the product obtained by reacting diketene or an equivalent acetoacetoxylating agent with an hydroxyl functional silicone polyether, a hydroxyorganosilane, a hydroxyorganosiloxane, or an amine functional siloxane polymer.

* * * * *